United States Patent
Tamura (10) Patent No.: US 11,693,177 B2
(45) Date of Patent: Jul. 4, 2023

(54) PERIPHERAL LIGHT-EMITTING LINEAR LIGHT GUIDE MEMBER AND METHOD FOR MANUFACTURING THE SAME

(71) Applicant: Hitachi Metals, Ltd., Tokyo (JP)

(72) Inventor: Kenichi Tamura, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 0 days.

(21) Appl. No.: 17/707,262

(22) Filed: Mar. 29, 2022

(65) Prior Publication Data
US 2022/0317366 A1    Oct. 6, 2022

(30) Foreign Application Priority Data
Apr. 2, 2021    (JP) .................................. 2021-063812

(51) Int. Cl.
  *G02B 6/02*    (2006.01)
  *G02B 6/036*    (2006.01)
  *A61B 1/07*    (2006.01)

(52) U.S. Cl.
  CPC .......... *G02B 6/02147* (2013.01); *G02B 6/036* (2013.01); *A61B 1/07* (2013.01)

(58) Field of Classification Search
  CPC ...... G02B 6/02147; G02B 6/036; A61B 1/07; A61B 2018/2244; A61B 2018/2261; A61N 2005/063; A61N 5/0601
  See application file for complete search history.

(56) References Cited

U.S. PATENT DOCUMENTS

| | | | | |
|---|---|---|---|---|
| 5,908,415 A | * | 6/1999 | Sinofsky | A61L 2/10 606/7 |
| 2005/0165462 A1 | * | 7/2005 | Bays | A61N 5/0601 607/88 |
| 2013/0060188 A1 | * | 3/2013 | Bedwell | A61L 29/106 604/21 |
| 2018/0311508 A1 | * | 11/2018 | Ellingwood | A61M 25/00 |
| 2019/0076119 A1 | * | 3/2019 | Yang | A61B 8/12 |
| 2019/0275346 A1 | | 9/2019 | Maeda | |
| 2020/0083659 A1 | * | 3/2020 | Reeves-Hall | H01S 3/1301 |

FOREIGN PATENT DOCUMENTS

JP    2018-079136 A    5/2018

* cited by examiner

*Primary Examiner* — Ellen E Kim
(74) *Attorney, Agent, or Firm* — McGinn I.P. Law Group, PLLC

(57) ABSTRACT

A peripheral light-emitting linear light guide member is composed of an optical fiber including a core having an outer periphery surface exposed from a cladding at one end in a longitudinal direction, and a light-scattering member covering an entire periphery of the outer periphery surface at an exposed portion of the core over a predetermined axial length range. The light-scattering member scatters a light emitted from the outer periphery surface of the core. In the light-scattering member, light-scattering particles are dispersion-mixed with an optically transparent base material having a higher refractive index than a refractive index of the core. An amount of the light-scattering particles around an outer periphery of the core is higher at a distal end of the light-scattering member than at an end closer to the cladding.

9 Claims, 6 Drawing Sheets

PERIPHERAL LIGHT-EMITTING LINEAR LIGHT GUIDE MEMBER AND METHOD FOR MANUFACTURING THE SAME

CROSS-REFERENCE TO RELATED APPLICATIONS

The present patent application claims the priority of Japanese patent application No. 2021-063812 filed on Apr. 2, 2021, and the entire contents thereof are hereby incorporated by reference.

TECHNICAL FIELD

The present invention relates to a peripheral light-emitting linear light guide member equipped with an optical fiber and a light-scattering member, and the method for manufacturing the same.

BACKGROUND ART

Conventionally, for example, a catheter treatment has been performed by inserting an optical fiber catheter equipped with an optical fiber into a human body's lumen organs such as esophagus, bowel, or a vessel or heart, and treating an affected area by light emitted from a core of the optical fiber (see e.g., Patent Literature 1).

An irradiation probe for irradiation therapy described in Patent Literature 1 has a light-guiding part including a core positioned in a tubular cladding, and a light-scattering and irradiating part for scattering the light transmitted by the light-guiding part around an axis of the core in all directions. The light-scattering and irradiating part is formed, for example, by removing the cladding at a tip end of the optical fiber for a predetermined length and by adhering fine powder such as metal particles to a side surface of an exposed portion of the core.

CITATION LIST

Patent Literature

Patent Literature 1: JP2018-79136 A

SUMMARY OF THE INVENTION

For optical fiber catheters that scatter light around an outer periphery of the core over a predetermined axial length range, it is desirable that the intensity of light is highly uniform across the above axial length range for improved treatment accuracy and safety. However, if light-scattering particles such as metal particles are placed on the outer periphery of the core exposed from the cladding at a certain ratio along an axial direction, the intensity of light emitted from a part near the tip end of the core toward the outer periphery of the core will be weakened.

Therefore, the object of the present invention is to provide a peripheral light-emitting linear light guide member and its manufacturing method, which can improve the uniformity of light intensity in an axial direction, compared with the case where a constant ratio of light-scattering particles is placed around an outer periphery of a core exposed from a cladding.

Accordingly, so as to solve the above problem, one aspect of the invention provides: a peripheral light-emitting linear light guide member comprising:

an optical fiber including a core having an outer periphery surface exposed from a cladding at one end in a longitudinal direction, and a light-scattering member covering an entire periphery of the outer periphery surface at an exposed portion of the core over a predetermined axial length range, wherein the light-scattering member scatters a light emitted from the outer periphery surface of the core, wherein in the light-scattering member, light-scattering particles are dispersion-mixed with an optically transparent base material having a higher refractive index than a refractive index of the core, and wherein an amount of the light-scattering particles around an outer periphery of the core is higher at a distal end of the light-scattering member than at an end closer to the cladding.

Further, so as to solve the above problem, another aspect of the invention provides: a method for manufacturing the peripheral light-emitting linear light guide member according to claim 1, the method comprising:

exposing the outer periphery surface of the core from the cladding of the optical fiber;

preparing a liquid body, which becomes the light-scattering member by being cured;

positioning the optical fiber above the liquid body in such a manner that the core protruding from an end of the cladding droops vertically;

relatively moving the core and the liquid body vertically, moving a part in the axial direction of the core downward from a liquid surface of the liquid body, and pulling up the core from the liquid body; and curing the liquid body being attached to the core by raising the core.

Effects of the Invention

According to the peripheral light-emitting linear light guide member and its manufacturing method of the present invention, it is possible to improve the uniformity of light intensity in the axial direction, compared with the case where the constant ratio of light-scattering particles is placed around the outer periphery of the core exposed from the cladding.

BEST MODE FOR CARRYING OUT THE INVENTION

Embodiment

Figure 1:
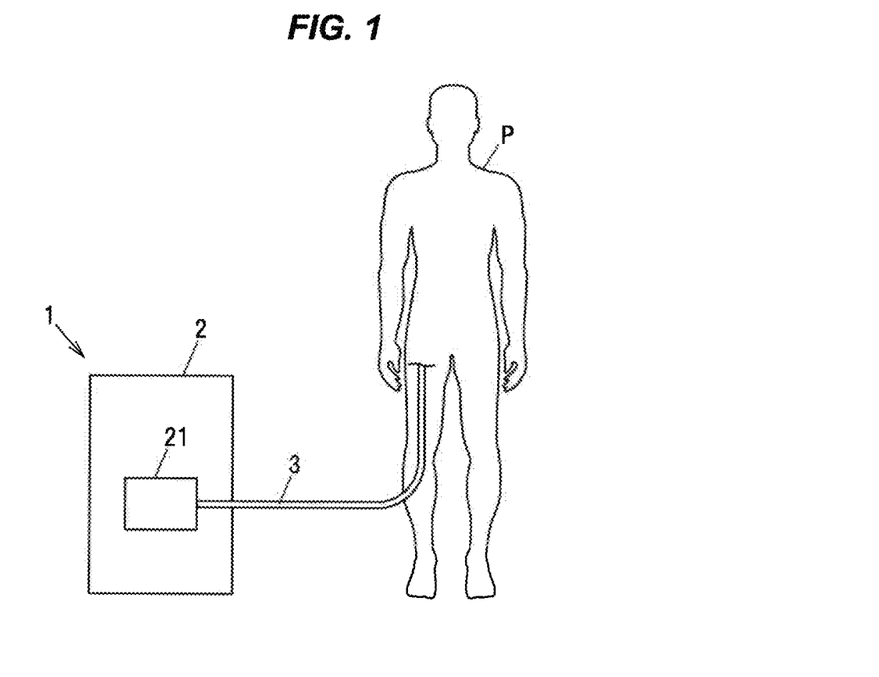
FIG. 1 is a schematic diagram showing a treatment device including a catheter configured with a peripheral light-emitting linear light guide member in an embodiment according to the present invention, together with a patient being treated.

FIG. 1 is a schematic diagram showing a treatment device 1 using a peripheral light-emitting linear light guide member 3 in an embodiment according to the present invention as a catheter together with a patient P being treated. The treatment device 1 includes a main body 2, and the peripheral light-emitting linear light guide member 3. A tip end (i.e., distal end) of the peripheral light-emitting linear light guide member 3 is inserted into the patient P. The main body 2 includes a light source 21 that emits laser light. The laser light generated by the light source 21 is incident to a base end (i.e., proximal end) of the peripheral light-emitting linear light guide member 3.

<Configuration of the Peripheral Light-Emitting Linear Light Guide Member>

Figure 2:
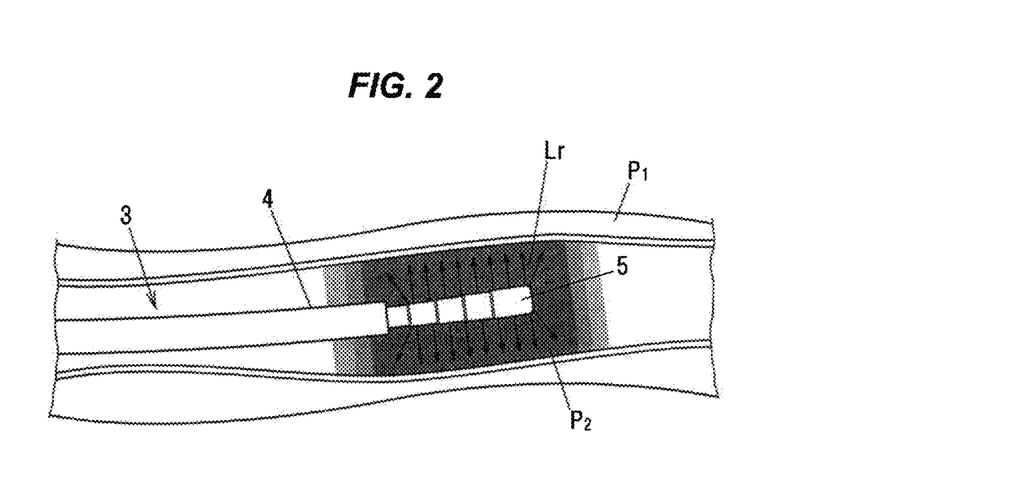
FIG. 2 is a schematic diagram showing a tip end of the catheter inserted into the patient.

FIG. 2 is a schematic diagram showing the tip end of the peripheral light-emitting linear light guide member 3 being inserted into the patient P. In FIG. 2, a vessel $P_1$ of the patient P is partially cut out, and the tip end of the peripheral light-emitting linear light guide member 3 being inserted into the vessel $P_1$ is shown. The scattered laser light LR emitted from the peripheral light-emitting linear light guide member 3 irradiates a treated site $P_2$ and reacts with the drugs contained in the treated site $P_2$. This provides intravascular laser treatment.

Figure 3A:
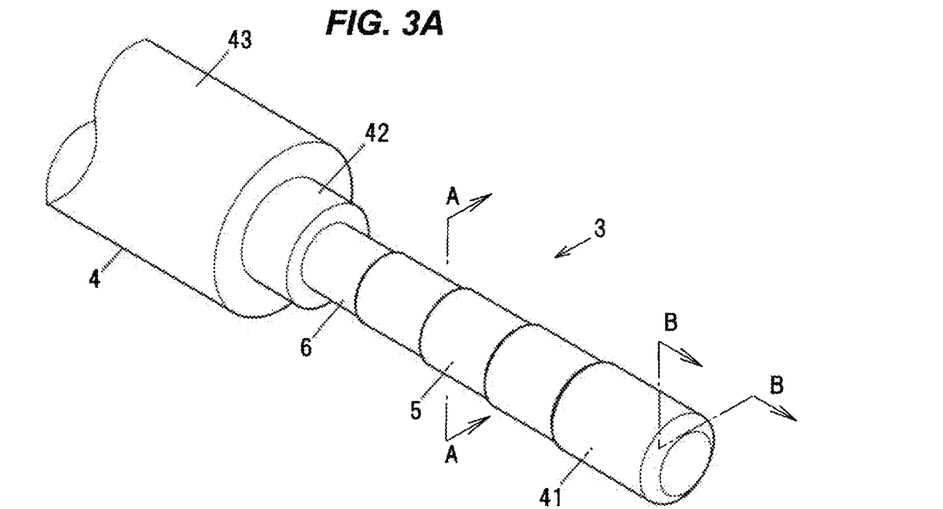
FIG. 3A is a perspective view of one end of the peripheral light-emitting linear light guide member.
Figure 3B:
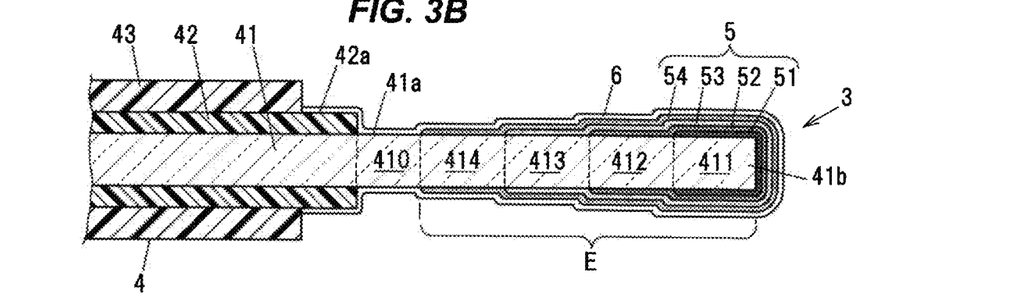
FIG. 3B is a cross-sectional view along an axial direction of the peripheral light-emitting linear light guide member taken along a line A-A in FIG. 3A.
Figure 3C:
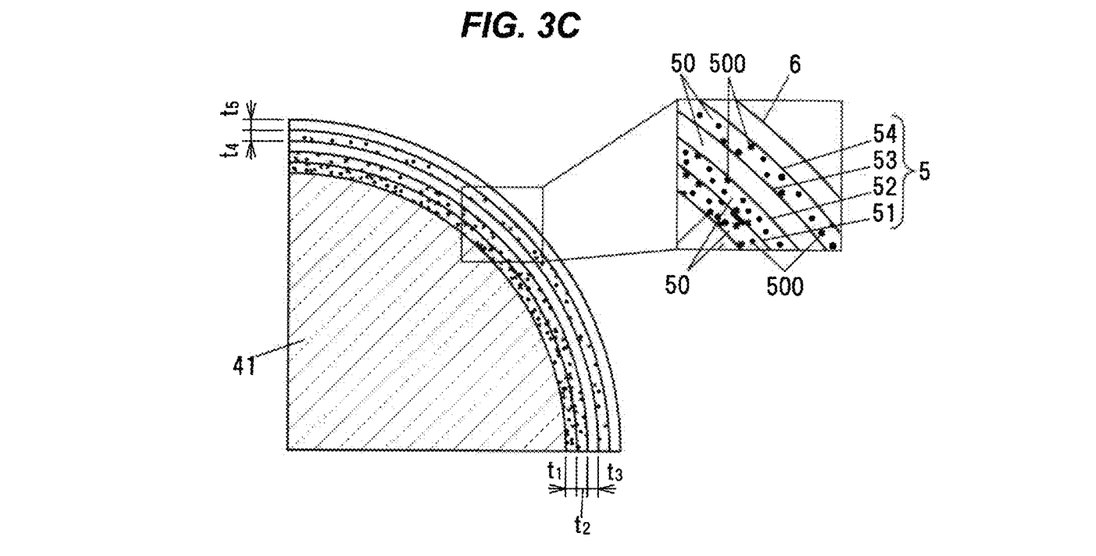
FIG. 3C is a cross-sectional view along a radial direction of the peripheral light-emitting linear light guide member taken along a line B-B in FIG. 3A.

FIG. 3A is a perspective view of one end of the peripheral light-emitting linear light guide member 3. FIG. 3B is a cross-sectional view along an axial direction of the peripheral light-emitting linear light guide member 3 taken along a line A-A in FIG. 3A. FIG. 3C is a cross-sectional view along a radial direction of the peripheral light-emitting linear light guide member 3 taken along a line B-B in FIG. 3A.

The peripheral light-emitting linear light guide member 3 includes an optical fiber 4, which directs the laser light generated by the light source 21 to the treated site $P_2$, a light-scattering member 5 located at one end of the optical fiber 4, and a protective coating layer 6, which covers the light-scattering member 5. The optical fiber 4 includes a core 41, a cladding 42, and a sheath 43. At one end in a longitudinal direction of the optical fiber 4, an outer periphery surface 42a of the cladding 42 is exposed from the sheath 43, and an outer periphery surface 41a of the core 41 is exposed from the cladding 42.

The light-scattering member 5 covers the entire circumference of the outer periphery surface 41a of the core 41 exposed from the cladding 42, over a predetermined axial length range. The axial length of the core 41 at the portion covered by the light-scattering member 5 is, e.g., 1 to 5 cm. A portion in the longitudinal direction of the core 41 is an uncovered portion 410 which is neither covered by the cladding 42 nor the light-scattering member 5. The protective coating layer 6 has optical transparency and covers the light-scattering member 5, the uncovered portion 410 of the core 41, and the cladding 42 at the portion exposed from the sheath 43.

In the present embodiment, the core 41 is composed of quartz glass and the cladding 42 is composed of polymer. The sheath 43 is composed of a fluorine resin, more specifically ETFE (ethylene tetrafluoroethylene copolymer). A diameter of the core 41 is, e.g., 200 μm. A refractive index of the core 41 is higher than a refractive index of the cladding 42, and the light that propagates the core 41 in the cladding 42 is totally reflected at an interface with the cladding 42. In the portion where the core 41 is exposed from the cladding 42, the light is emitted from the outer periphery surface 41a of the core 41.

The light-scattering member 5 is configured to emit the light emitted from the outer periphery surface 41a of the core 41. The light-scattering member 5 is composed of an optically transparent base material 50 which has a higher refractive index than the core 41 and a large number of light-scattering particles 500 being dispersion-mixed with the base material 50. In this case, "being dispersion-mixed" means that the light-scattering particles 500 are evenly distributed in the base material 50 in such a manner that the light-scattering particles 500 do not get stuck in part in the base material 50. In the present embodiment, the base material 50 is composed of a thermosetting (i.e., thermocuring) resin. The light-scattering particles 500 are fine particles that cannot be recognized by the naked eye, and FIG. 3C exaggerates the size of the light-scattering particles 500 for the purpose of explanation.

The refractive index of the base material 50 is higher than the refractive index of the core 41, and the light emitted from the outer periphery surface 41a of the core 41 enters the light-scattering member 5. In the present embodiment, the base material 50 is silicone resin, and its refractive index is, e.g., 1.52. The refractive index of the core 41 is, e.g., 1.46. The refractive index of the protective coating layer 6 is equal to the refractive index of the light-scattering member 5 or higher than the refractive index of the light-scattering member 5.

The light-scattering particle 500 is a metal particle that reflects the light incident to the light-scattering member 5. In the present embodiment, titanium oxide ($TiO_2$) is used as the light-scattering particle 500. However, the present invention is not limited thereto. Fine metal powders of aluminum oxide (alumina), iron, silver, copper, or alloys thereof may be used as the light-scattering particles 500.

The light-scattering member 5 has a multi-layer structure composed of several layers, where at least a part of these layers overlaps in the radial direction of the core 41. In the present embodiment, the number of layers of the light-scattering member 5 is four. In the core 41 at the tip end 41b, the four layers overlap in the radial direction. The four layers are, starting from the inside, a first light-scattering layer 51, a second light-scattering layer 52, a third light-scattering layer 53, and a fourth light-scattering layer 54. The first to fourth light-scattering layers 51 to 54 are dispersion-mixed with a large number of light-scattering particles 500 in each of the base materials 50.

As shown in FIG. 3C, thicknesses $t_1$ to $t_4$ of the first to fourth light-scattering layers 51 to 54 in the radial direction of the core 41 are the same as each other. The thicknesses $t_1$ to $t_4$ are, e.g., 5 to 10 μm. A thickness $t_5$ of the protective coating layer 6 is the same as $t_1$ to $t_4$ as an example, but it can be different from $t_1$ to $t_4$.

As shown in FIG. 3B, when the axial length range E of the core 41 covered by the light-scattering member 5 is divided into first to fourth regions 411 to 414, depending on the number of layers (four in this case). In the first region 411 on a distalmost side of the core 41, the first to fourth light-scattering layers 51 to 54 are formed around the outer periphery of the core 41, while in the fourth region 414 on a proximalmost side which is closest to the cladding 42, only the fourth light-scattering layer 54 is formed around the outer periphery of the core 41. In the second region 412 adjacent to the first region 411, the second to fourth light-scattering layers 52 to 54 are formed around the outer periphery of the core 41, and in the third region 413 adjacent to the fourth region 414, the third and fourth light-scattering layers 53, 54 are formed around the outer periphery of core 41. The outer periphery surface 41a of the core 41 and the first to fourth light-scattering layers 51 to 54 are closely in contact with each other without gaps.

According to this multi-layer structure, the thickness of the light-scattering member 5 in the radial direction of the core 41 is thicker in the outer periphery of the first region 411 (at the tip end 41b on the distalmost side of the core 41) than in the outer periphery of the fourth region 414 (at the proximalmost side, which is closest to the cladding 42). In addition, the amount of the light-scattering particles 500 around the outer periphery of the core 41 is higher in the outer periphery of the first region 411 (at the tip end 41b on the distalmost side of the core 41) than in the fourth region 414 (at the proximalmost side, which is closest to the cladding 42).

The mixing ratios of the light-scattering particles 500 to the base material 50 in the first to fourth light-scattering layers 51 to 54 are different from each other. In the present embodiment, when concentrations of the light-scattering particles 500 in the first to fourth light-scattering layers 51 to 54 are $C_1$ to $C_4$, the concentration $C_1$ in the first light-scattering layer 51 is, e.g., 20 mg/ml, the concentration $C_2$ in the second light-scattering layer 52 is, e.g., 10 mg/ml, and the concentration $C_3$ in the third light-scattering layer 53 is, e.g., 0 mg/ml, and the concentration $C_4$ in the fourth light-scattering layer is, e.g., 7 mg/ml. In other words, in the present embodiment, the relationship between the concentrations $C_1$ to $C_4$ of the light-scattering particles 500 in the first to fourth light-scattering layers 51 to 54 is expressed as $C_1>C_2>C_4>C_3$.

Thus, in the present embodiment, the first light-scattering layer 51, which has the highest mixing ratio of the light-scattering particles 500 among the first to fourth light-scattering layers 51 to 54, is formed in the first region 411 at the distalmost side of the core 41.

In the present embodiment, the concentration $C_4$ in the fourth light-scattering layer 54 formed in contact with the outer periphery surface 41a of the core 41 in the fourth region 414 is higher than the concentration $C_3$ of the third light-scattering layer 53 formed in contact with the outer periphery surface 41a of the core 41 in the third region 413. For example, it was observed that the intensity of light emitted from the light-scattering member 5 peaked at a region being slightly distant along the axial direction from the proximal most side, which is closest to the cladding 42 of the light-scattering member 5 when the concentration $C_3$ and the concentration $C_4$ were equal. It is a result of the adjustment in such a manner as to improve the uniformity of the intensity of light emitted from the light-scattering member 5 and to improve the rise in intensity of light at the proximalmost side closest to the cladding 42 of the light-scattering member 5. In the above example, the concentration $C_3$ in the third light-scattering layer 53 is 0 mg/ml, and the third light-scattering layer 53 does not include (i.e., is free of) the light-scattering particles 500. However, the present invention is not limited thereto, and the third light-scattering layer 53 may include the light-scattering particles 500. However, even in this case, it is desirable that the concentration $C_3$ in the third light-scattering layer 53 is lower than the concentration $C_4$ in the fourth light-scattering layer 54.

In this case, the number of layers of the light-scattering member 5 is four. However, the number of layers of the light-scattering member 5 is not limited to four, but it may be two, three, or five or more. If the number of layers is n (where n is a natural number of 2 or more) and the axial length range E of the core 41 is divided into n regions according to the number of layers, the number of layers in the distalmost region of the core 41 is n, and the number of layers in the proximalmost region which is closest to the cladding 42 is 1.

In addition, the light-scattering member 5 may have a single layer structure with a uniform ratio of the light-scattering particles 500 to the base material 50, not just a multi-layer structure. In this case, the thickness of the light-scattering member 5 in the radial direction of the core 41 is set to be thicker at the distalmost end, i.e., the tip end 41b of the core 41 than at the proximalmost end, i.e., the end closest to the cladding 42, so that the amount of the light-scattering particles 500 around the outer periphery of the core 41 at the distalmost end, i.e., the tip end 41b of the core 41 is greater than at the proximalmost end, i.e., the end closest to the cladding 42.

<Method for Manufacturing the Peripheral Light-Emitting Linear Light Guide Member 3>

Next, a method for manufacturing the peripheral light-emitting linear light guide member 3 will be explained. The method for manufacturing the peripheral light-emitting linear light guide member 3 includes an optical fiber processing step of exposing the outer periphery surface 41a of the core 41 from the cladding 42 of the optical fiber 4, a preparation step of preparing a liquid body, which becomes the light-scattering member 5 by being cured, a positioning step of positioning the optical fiber 4 above the liquid body in such a manner that the core 41 protruding from an end of the cladding 42 droops vertically, a moving step of relatively moving the core 41 and the liquid body vertically, moving a part in the axial direction of the core 41 downward from a liquid surface of the liquid body, and pulling up the core 41 from the liquid body, and a curing step of curing the liquid body being attached to the core 41 by raising the core 41.

Figure 4A:
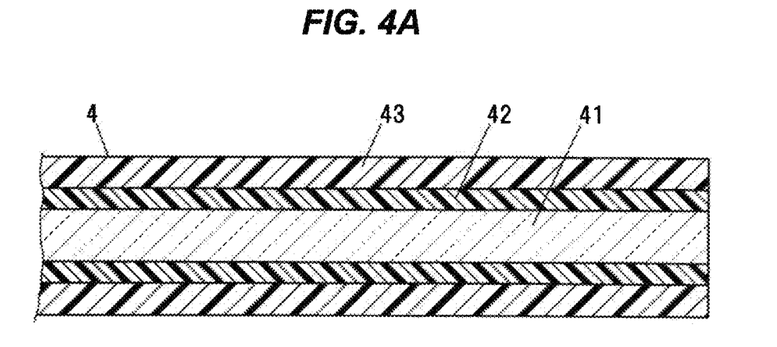
FIGS. 4A to 4C are explanatory diagrams showing a processing step of an optical fiber.
Figure 4B:
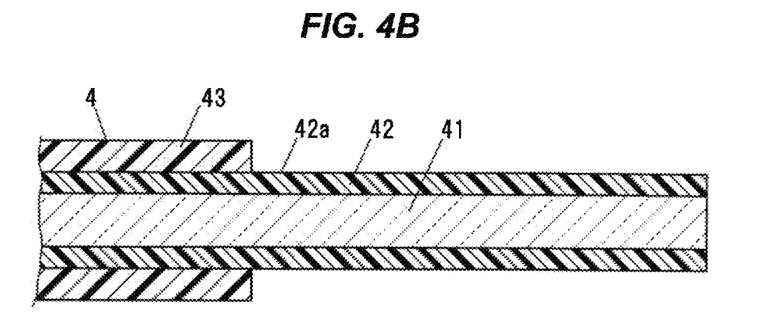
Figure 4C:
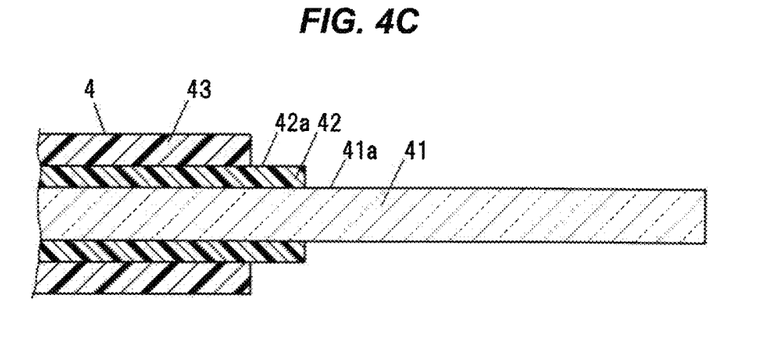
Figure 5A:
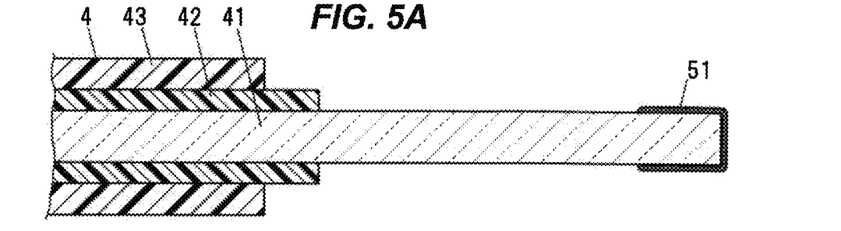
FIGS. 5A to 5D are explanatory diagrams showing a sequential formation of first to fourth light-scattering layers and a protective coating layer around an outer periphery of an exposed core.
Figure 5B:
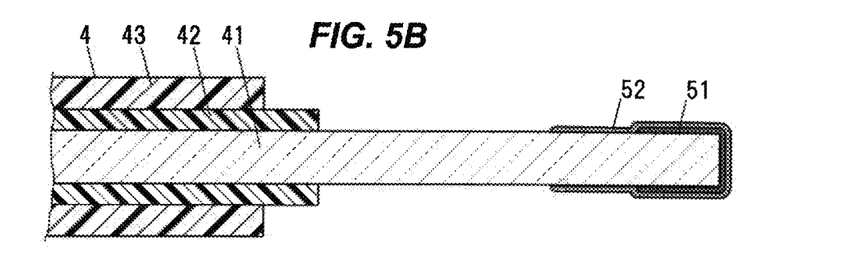
Figure 5C:
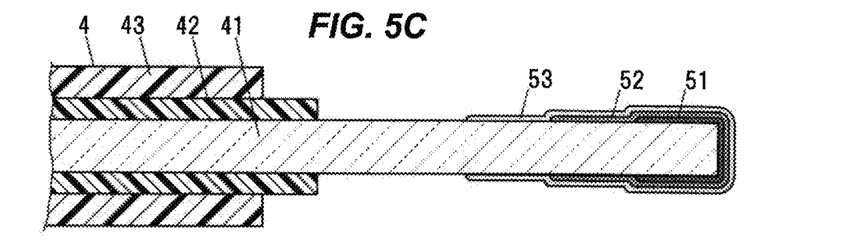
Figure 5D:
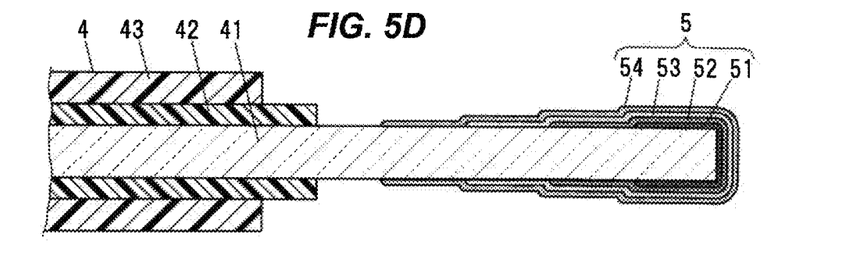
Figure 5E:
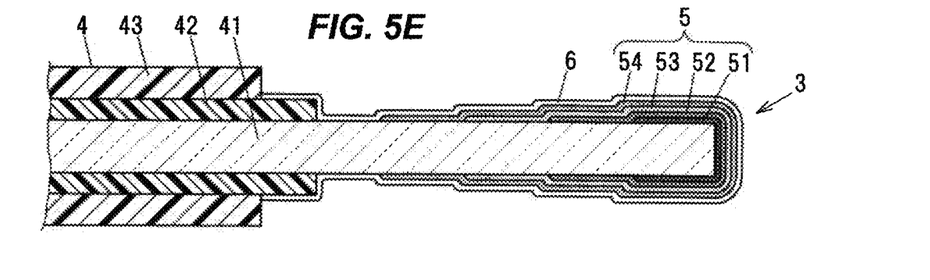

FIGS. 4A to 4C are explanatory diagrams showing the optical fiber processing step. FIG. 4A shows the optical fiber 4 before being processed. In this situation, the outer periphery of the core 41 is covered by the cladding 42 and the outer periphery of the cladding 42 is covered by the sheath 43. FIG. 4B shows the state where the sheath 43 is removed from the axial end over a predetermined length range, and the outer periphery surface 42a of the cladding 42 is exposed. FIG. 4C shows the state where the cladding 42 at the region exposed from the sheath 43 is removed from the axial end over a predetermined length range, and the outer periphery surface 41a of the core 41 is exposed.

FIGS. 5A to 5D are explanatory diagrams showing a sequential formation of first to fourth light-scattering layers 51 to 54 and the protective coating layer 6 around the outer periphery of the exposed core 41. As shown in FIGS. 5A to 5D, the light-scattering member 5 is formed as follows. The first light-scattering layer 51 is formed around the outer periphery of the first region 411 of the core 41, and then the second light-scattering layer 52 is formed around the outer peripheries of the first light-scattering layer 51 and the second region 412 of the core 41. Thereafter, the third light-scattering layer 53 is formed around the outer peripheries of the second light-scattering layer 52 and the third region 413 of the core 41, and the fourth light-scattering layer 54 is formed around the outer peripheries of the third light-scattering layer 53 and the fourth region 414 of the core 41.

Figure 6A:
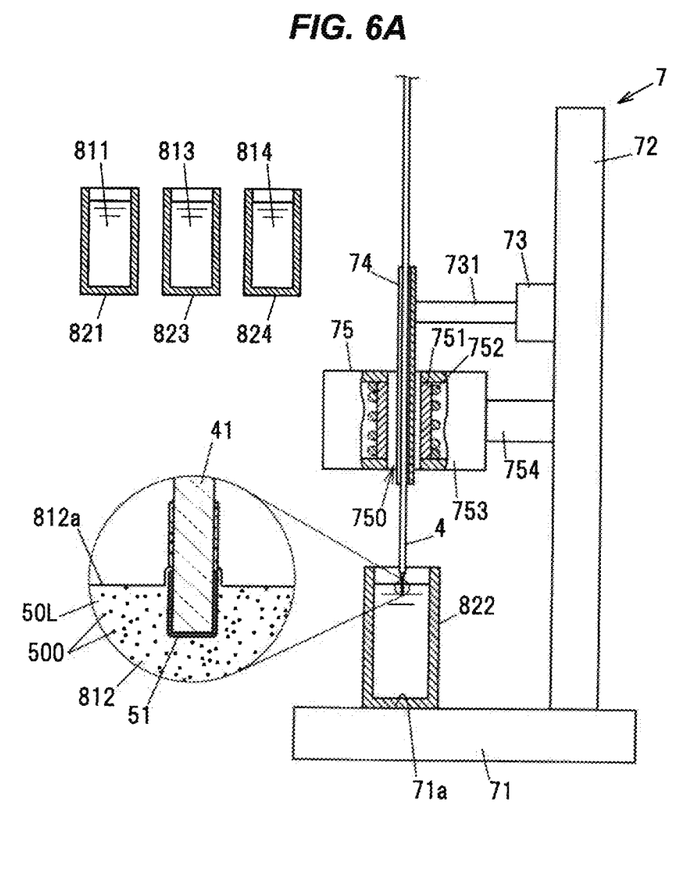
FIGS. 6A and 6B are schematic diagrams showing a light-scattering layer formation device for forming the first to fourth light-scattering layers.
Figure 6B:
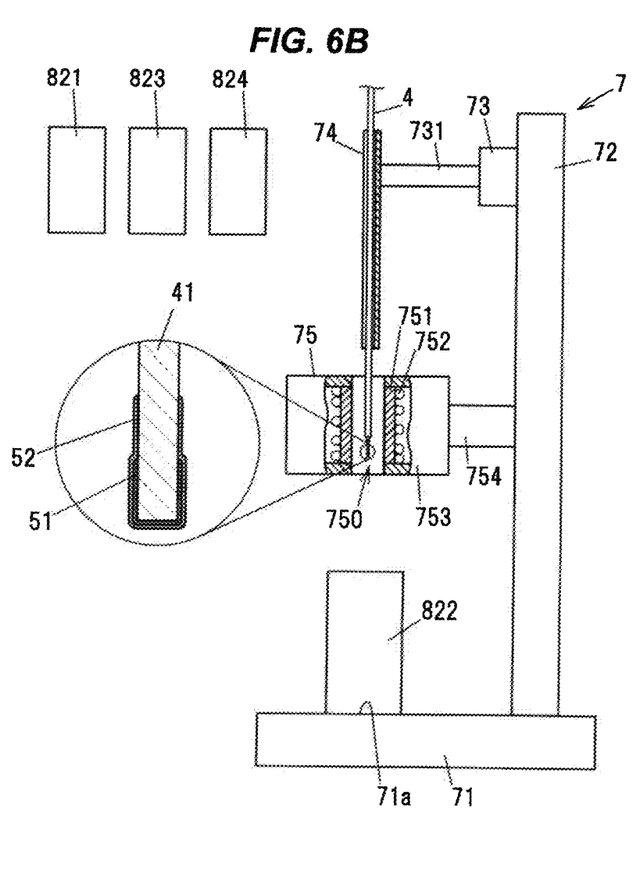

FIGS. 6A and 6B are schematic diagrams showing a light-scattering layer formation device 7 for forming the first to fourth light-scattering layers 51 to 54. In FIGS. 6A and 6B, the drawing up and down directions are vertically up and down directions. The light-scattering layer formation device 7 includes a base plate 71, a pole 72 mounted vertically to the base plate 71, a lifting platform 73, which can be moved up and down relative to the pole 72, a holder 74 for holding the optical fiber 4, and a heater 75 being secured to the pole 72.

The lifting platform 73 is moved up and down with an actuator (not shown) to the pole 72. For example, the actuator can be configured to convert the rotation of an electric motor into a linear motion by means of a ball screw, for example. The lifting platform 73 has a support 731 which supports the holder 74, and the holder 74 is supported by the support 731.

The holder 74 holds the optical fiber 4 in the portion covered by the sheath 43 in the vertical direction over a predetermined length range. According to this configuration, the core 41 protruding from the end of the cladding 42 is positioned to hang vertically downward in the positioning step. The holder 74 moves up and down with the lifting platform 73 while holding the optical fiber 4.

The heater 75 includes a mating hole 750 which allows the optical fiber 4 to be inserted up and down. Around the mating hole 750, a cylindrical radiation member 751 radiates infrared light. By heating the radiation member 751 by electrical heating wire 752, the infrared light is emitted into the mating hole 750. This enables uniform heating of the portion around the core 41 of the optical fiber 4 from all directions. The radiation member 751 and the electrical heating wire 752 are contained in a casing member 753. The casing member 753 is connected to the pole 72 by a connecting arm 754.

During the preparation step, several types of liquid bodies (first to the fourth liquid bodies 811 to 814) with different ratios of the light-scattering particles 500 are prepared. The first liquid body 811 becomes the first light-scattering layer 51 by curing, and the second liquid body 812 becomes the second light-scattering layer 52 by curing. In addition, the third liquid body 813 becomes the third light-scattering layer 53 by curing, and the fourth liquid body 814 becomes the fourth light-scattering layer 54 by curing.

The first to fourth liquid bodies 811 to 814 are dispersion-mixed with a large number of the light-scattering particles 500 in the liquid base material SOL before being cured. The liquid base material SOL is liquid at room temperature before the heating step, and is cured by heating with the heater 75, resulting in the base material 50 in a solid state. The concentration of the light-scattering particles 500 in the first to fourth liquid bodies 811 to 814 is the concentration according to the above relationship $C_1 > C_2 > C_4 > C_3$.

The first to fourth liquid bodies 811 to 814 are contained in first to fourth containers 821 to 824, respectively. The first to fourth containers 821 to 824 are cup-shaped with the upper opening. FIG. 6A shows cross-sectional views of the first to fourth containers 821 to 824 of the first and fourth liquid bodies 811 to 814. FIGS. 6A and 6B show that the second container 822 is mounted on a mounting surface 71a of the base plate 71 below the heater 75.

When forming light-scattering member 5, the moving step and curing step are repeated for each of the first to fourth liquid bodies 811 to 814. In the present embodiment, the light-scattering member 5 has a four-layer structure, and the moving step and the curing step are repeated four times for each liquid body. The first to fourth liquid bodies 811 to 814 are sequentially mounted on the mounting surface 71a of the base plate 71 each time when the moving step and curing step are finished.

In the moving step, a part in the axial direction of the core 41 is moved downward below the liquid level of the first to fourth liquid bodies 811 to 814 by the downward movement of the lifting platform 73, and then the core 41 is raised from the first to fourth liquid bodies 811 to 814. The liquid base material SOL is viscous, and when the lifting platform 73 moves upwards, the core 41 is raised with the base material SOL attached to the outer periphery of the core 41 because of its viscosity. FIG. 6A shows the core 41 being pulled upwards from a liquid level 812a of the second liquid body 812.

When raising the core 41, the lifting platform 73 is adjusted to be raise at a low speed e.g., 0.02 mm/sec, in such a manner that the base material SOL is attached to the core 41 with a thickness as uniform as possible. The raising speed of the core 41 is preferably 0.1 mm/sec or less, more preferably 0.05 mm/sec or less. FIG. 6A shows that the second liquid body 812 adheres with a uniform thickness to the outer peripheries of the first light-scattering layer 51 and the second region 412 of the core 41.

In the curing step, as shown in FIG. 6B, the lifting platform 73 is raised until the core 41 exposed from the cladding 42 is located into the mating hole 750 of the heater 75. The first to fourth liquid bodies 811 to 814 attached during the moving step are heated and cured by infrared light emitted from the radiation member 751.

Then, after forming the first to fourth light-scattering layers 51 to 54 around the outer periphery of the core 41, the protective coating layer 6 is formed to provide the peripheral light-emitting linear light guide member 3. The protective coating layer 6 may be formed in the same way as the first to fourth light-scattering layers 51 to 54, for example, but the present invention is not limited thereto. The protective coating layer 6 may be formed by a process different from the steps for forming the first to fourth light-scattering layers 51 to 54.

<Configuration of a Peripheral Light-Emitting Linear Light Guide Member 3 in Comparative Example>

Figure 7:
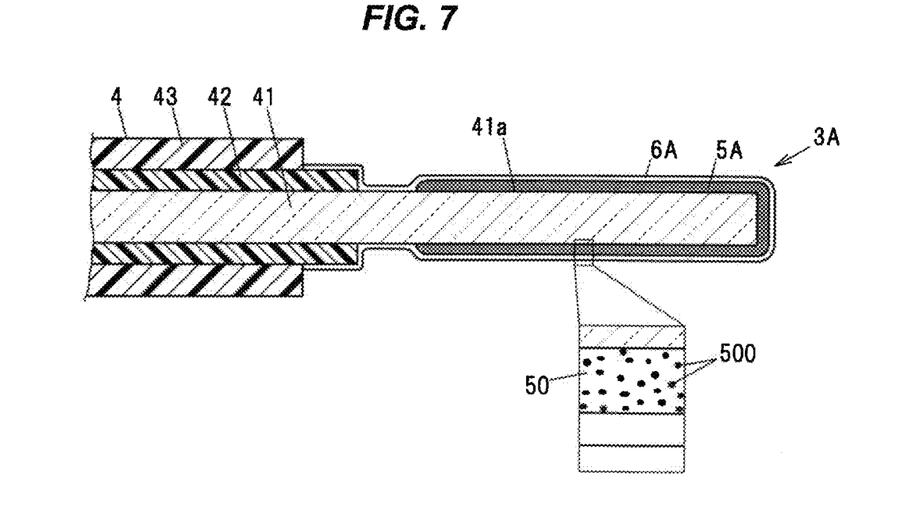
FIG. 7 is a cross-sectional view showing a peripheral light-emitting linear light guide member in a comparative example.

FIG. 7 is a cross-sectional view of a peripheral light-emitting linear light guide member 3A in the comparative example. This peripheral light-emitting linear light guide member 3A includes an optical fiber 4 including a core 41 with an outer periphery surface 41a exposed from a cladding 42, similarly to the peripheral light-emitting linear light guide member 3 in the above embodiment. The entire outer periphery surface 41a of the core 41 is covered by a light-scattering member 5A over a predetermined axial length range, but a configuration of the light-scattering member 5A differs from that of the light-scattering member 5 in the above embodiment.

The light-scattering member 5A of the peripheral light-emitting linear light guide member 3A has a single-layer structure, with the core 41 having a constant thickness in a radial direction throughout the entire axial direction. Further, as in the above embodiment, in the light-scattering member 5A, a large number of the light-scattering particles 500 are dispersion-mixed with the base material 50. The ratio of the light-scattering particles 500 to the base material 50 in the light-scattering member 5A is uniform throughout the entire axial direction. The outer periphery of the light-scattering member 5A is covered by a protective coating layer 6A.

<Distribution of Light Intensity in the Peripheral Light-Emitting Linear Light Guide Member 3 in the Embodiment and the Peripheral Light-Emitting Linear Light Guide Member 3A in the Comparative Example>

Figure 8:
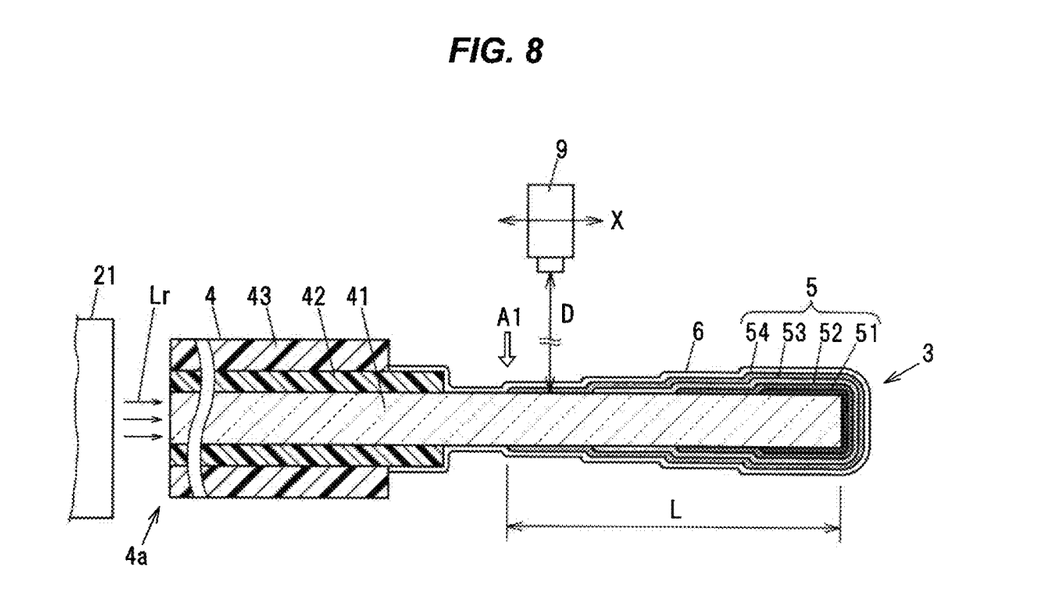
FIG. 8 is an explanatory diagram showing a method for measuring an axial distribution of the light intensity of the peripheral light-emitting linear light guide member in the present embodiment and a peripheral light-emitting linear light guide member in the comparative example.

FIG. 8 is an explanatory diagram showing a method for measuring an axial distribution of the light intensity of the peripheral light-emitting linear light guide member 3 in the present embodiment and the peripheral light-emitting linear light guide member 3A in the comparative example. FIG. 8 shows the state of the measurement of the peripheral light-emitting linear light guide member 3 as an example, but the distribution of light intensity is similarly measured for the peripheral light-emitting linear light guide member 3A in the comparative example.

In this measurement method, the laser light LR generated by the light source 21 is injected into the core 41 from the base end (i.e., proximal end) 4a of the optical fiber 4, and the intensity of light emitted from the light-scattering member 5, 5A in the radial direction of the core 41 is measured by an optical power meter 9. A distance D between the optical power meter 9 and the core 41 is 2.5 mm or 5.0 mm During the measurement, the optical power meter 9 is moved in X-direction parallel to the core 41 and the light intensity is measured in multiple X-direction positions. In this case, a length L of the light-scattering member 5, 5A in the axial direction of the core 41 is 20 mm.

Next, the results of the measurement of the optical intensity distribution in the peripheral light-emitting linear light guide member 3 in the embodiment, and in the peripheral light-emitting linear light guide member 3A in the comparative example will be explained.

The uniformity of the light intensity in the axial direction of the core 41 was improved in the peripheral light-emitting linear light guide member 3 in the present embodiment, compared with the peripheral light-emitting linear light guide member 3A in the comparative example. Specifically, when the position of the optical power meter 9 in the X-direction is x, the peripheral light-emitting linear light guide member 3A in the comparative example had its peak intensity around x=5 mm, and the light intensity decreased as being closer to the tip end (i.e., distal end) 41b of the core 41. On the other hand, in the peripheral light-emitting linear light guide member 3, the light intensity was the maximum value near the tip end (i.e., distal end) 41b, resulting in a flat distribution of light intensity as a whole. This is due to the following reasons.

The light emitted from the core 41 and injected into the light-scattering member 5, 5A passes through the base material 50 without hitting the light-scattering particles 500. When the light reaches an interface between the protective coating layer 6, 6A and the atmosphere, the proportion of the light reflected at this interface and then re-injected into the core 41 is large. It is because that an angle of the light transmitted from the light source 21 to the core 41 with respect to the axial direction of the core 41 is shallow. However, when the light injected into the light-scattering member 5, 5A hits the light-scattering particles 500, the light-scattering particles 500 diffuse the light, and the reflected light is incident at a relatively large angle to the interface between the protective coating layer 6, 6A and the atmosphere. As a result, the reflected light being reflected by the light-scattering particles 500 is likely to be emitted outward from the light-scattering member 5, 5A and the protective coating layer 6, 6A.

In the peripheral light-emitting linear light guide member 3A in the comparative example, the thickness of the light-scattering member 5A and the ratio of the light-scattering particles 500 are uniform across the entire part in the axial direction. Therefore, the intensity distribution of the light measured by the optical power meter 9 was roughly consistent with the intensity distribution of the light entering from the core 41 to the light-scattering member 5A. The light in the core 41 gradually weakens as it approaches the tip end (i.e., distal end) 41b due to its divergence toward the outside, so the intensity of the light emitted from the light-scattering member 5A gradually decreased as being closer to the tip end (i.e., distal end) 41b of the core 41.

On the other hand, in the peripheral light-emitting linear light guide member 3 in the present embodiment, the amount of the light-scattering particles 500 around the outer periphery of the core 41 is less near a reference position while the amount of the light-scattering particles 500 is much near the tip end (i.e., distal end) 41b of the core 41. Therefore, the light emitted from the fourth region 414 near the reference position of the core 41 to the light-scattering member 5 is easily reflected back to the core 41 at the interface between the protective coating layer 6 and the atmosphere. On the other hand, the light emitted from the first region 411 near the tip end (i.e., distal end) 41b of the core 41 is reflected by the light-scattering particles 500, and is easily radiated outside the protective coating layer 6. In other words, the overall flat light intensity distribution can be obtained by balancing the intensity of light within the core 41 and the ease of radiation toward the outside of the light-scattering member 5 and the protective coating layer 6.

(Operations and Effects of the Embodiment)

According to the present embodiment, it is possible to increase the uniformity of the intensity of light emitted from the light-scattering member 5. In addition, because the light-scattering member 5 has a multi-layered structure, it is possible to set the amount of the light-scattering particles 500 around the outer periphery of the core 41 appropriately for the respective regions depending on the number of layers.

In particular, in the present embodiment, the first light-scattering layer 51, which has the highest mixing ratio of the light-scattering particles 500, is formed around the outer periphery of the first region 411 at the distalmost end of the core 41, so even though the amount of the light emitted from the first region 411 of the core 41 to the light-scattering member 5 is small, it is possible to increase the proportion of the light emitted from the first region 411 to the outside of the light-scattering member 5 and the protective coating layer 6.

In addition, according to the method for manufacturing the peripheral light-emitting linear light guide member 3 in the present embodiment, the thicknesses in the radial direction of the first to fourth light-scattering layers 51 to 54 can be uniformly provided in both the axial direction and the circumferential direction.

SUMMARY OF THE EMBODIMENT

Technical ideas understood from the embodiment will be described below citing the reference signs, etc., used for the embodiments. However, each reference sign, etc., described below is not intended to limit the constituent elements in the claims to the members, etc., specifically described in the embodiments.

[1] A peripheral light-emitting linear light guide member 3 comprising: an optical fiber 4 including a core 4a having an outer periphery surface 41a exposed from a cladding 42 at one end in a longitudinal direction, and a light-scattering member 5 covering an entire periphery of the outer periphery surface 41a at an exposed portion of the core 41 over a predetermined axial length range, wherein the light-scattering member 5 scatters a light emitted from the outer periphery surface 41a of the core 41, wherein in the light-scattering member 5, light-scattering particles 500 are dispersion-mixed with an optically transparent base material 50 having a higher refractive index than a refractive index of the core 41, and wherein an amount of the light-scattering particles 500 around an outer periphery of the core 41 is higher at a distal end of the light-scattering member 5 than at an end closer to the cladding 42.

[2] The peripheral light-emitting linear light guide member 3 as described in [1], wherein the base material 50 is silicone resin, and the light-scattering particles 500 are metal particles that reflect light.

[3] The peripheral light-emitting linear light guide member 3 as described in [1] or [2], wherein a thickness of the light-scattering member 5 in a radial direction of the core 41 is thicker at the distal end of the core 41 than at the end closer to the cladding 42.

[4] The peripheral light-emitting linear light guide member 3 as described in any one of [1] to [3], wherein the light-scattering member 5 includes layers (i.e., the first to fourth light-scattering layers) 51 to 54 with different mixing ratios of the light-scattering particles 500 to the base material 50, and at least a portion of the layers overlap in the radial direction of the core 41.

[5] The peripheral light-emitting linear light guide member 3 as described in [4], wherein, when a number of the layers is n, where n is a natural number of 2 or more, and the predetermined axial length range E is divided into n regions (the first to fourth regions) 411 to 414 according to the number of layers, the number of layers in a distalmost region (the first region) 411 of the core 41 is n, and the number of layers in a region (the fourth region) 414 which is closest to the cladding 42 is 1.

[6] The peripheral light-emitting linear light guide member 3 as described in [5], wherein a layer 51 with a highest mixing ratio of the light-scattering particles 500 in the layers 51 to 54 is formed at a distalmost region of the n regions 411 to 414 of the core 41.

[7] A method for manufacturing the peripheral light-emitting linear light guide member 3 as described in any one of [1] to [6] comprising: an optical fiber processing step of exposing the outer periphery surface 41a of the core 41 from the cladding 42 of the optical fiber 4; a preparation step of preparing a liquid body (i.e., the first to fourth liquid bodies) 811 to 814, which becomes the light-scattering member 5 by being cured; a positioning step of positioning the optical fiber 4 above the liquid body 811 to 814 in such a manner that the core 41 protruding from an end of the cladding 42 droops vertically; a moving step of relatively moving the core 41 and the liquid body 811 to 814 vertically, moving a part in the axial direction of the core 41 downward from a liquid surface of the liquid body 811 to 814, and pulling up the core 41 from the liquid body 811 to 814; and a curing step of curing the liquid body 811 to 814 being attached to the core 41 by raising the core 41.

[8] The method for manufacturing the peripheral light-emitting linear light guide member 3 as described in [7], wherein, during the preparation step, plural types of liquid bodies 811 to 814 with different ratios of the light-scattering particles 500 are prepared, and wherein the moving step and the curing step are repeated for each of the plural types of liquid bodies 811 to 814.

[9] The method for manufacturing the peripheral light-emitting linear light guide member 3 as described in [7] or [8], wherein the base material 50 is a thermosetting resin, and wherein the curing step comprises heating the liquid body 811 to 814 to be cured.

Although the embodiment of the invention has been described, the invention according to claims is not to be limited to the embodiment described above. Further, please note that not all combinations of the features described in the embodiment are necessary to solve the problem of the invention. The invention can also be enforced by its modification and variation as necessity without deviating from its intended purpose.

The invention claimed is:

1. A peripheral light-emitting linear light guide member comprising:
    an optical fiber including a core having an outer periphery surface exposed from a cladding at one end in a longitudinal direction, and
    a light-scattering member covering an entire periphery of the outer periphery surface at an exposed portion of the core over a predetermined axial length range,
    wherein the light-scattering member scatters a light emitted from the outer periphery surface of the core,
    wherein in the light-scattering member, light-scattering particles are dispersion-mixed with an optically transparent base material having a higher refractive index than a refractive index of the core, and
    wherein an amount of the light-scattering particles around an outer periphery of the core is higher at a distal end of the light-scattering member than at an end closer to the cladding.

2. The peripheral light-emitting linear light guide member, according to claim 1, wherein the base material is silicone resin, and the light-scattering particles are metal particles that reflect light.

3. The peripheral light-emitting linear light guide member, according to claim 1, wherein a thickness of the light-scattering member in a radial direction of the core is thicker at the distal end of the core than at the end closer to the cladding.

4. The peripheral light-emitting linear light guide member, according to claim 1, wherein the light-scattering member includes layers with different mixing ratios of the light-scattering particles to the base material, and at least a portion of the layers overlap in the radial direction of the core.

5. The peripheral light-emitting linear light guide member, according to claim 4, wherein, when a number of the layers is n, where n is a natural number of 2 or more, and the predetermined axial length range E is divided into n regions according to the number of layers, the number of layers in a distalmost region of the core is n, and the number of layers in a region which is closest to the cladding is 1.

6. The peripheral light-emitting linear light guide member, according to claim 5, wherein a layer with a highest mixing ratio of the light-scattering particles in the layers is formed at a distalmost region of the n regions of the core.

7. A method for manufacturing the peripheral light-emitting linear light guide member according to claim 1, the method comprising:
- exposing the outer periphery surface of the core from the cladding of the optical fiber;
- preparing a liquid body, which becomes the light-scattering member by being cured;
- positioning the optical fiber above the liquid body in such a manner that the core protruding from an end of the cladding droops vertically;
- relatively moving the core and the liquid body vertically, moving a part in the axial direction of the core downward from a liquid surface of the liquid body, and pulling up the core from the liquid body; and
- curing the liquid body being attached to the core by raising the core.

8. The method for manufacturing the peripheral light-emitting linear light guide member, according to claim 7, wherein, during the preparation step, plural types of liquid bodies with different ratios of the light-scattering particles are prepared, and wherein the moving step and the curing step are repeated for each of the plural types of liquid bodies.

9. The method for manufacturing the peripheral light-emitting linear light guide member, according to claim 7, wherein, the base material is a thermosetting resin, and wherein the curing step comprises heating the liquid body to be cured.

\* \* \* \* \*